(12) United States Patent
Bleuse et al.

(10) Patent No.: US 6,309,604 B1
(45) Date of Patent: Oct. 30, 2001

(54) APPARATUS COMBINING SPECTROPHOTOMETRY AND FLAME IONISATION DETECTION FOR ANALYSING A GAS COMPOSITION

(75) Inventors: Patrick Bleuse, Bois d'Arcy; Pierre Clausin, Ville d'Avray; Gilles Guene, Elancourt; Henri Lancelin, Athis-Mons, all of (FR)

(73) Assignee: Proengin S.A. (FR)

( * ) Notice: Subject to any disclaimer, the term of this patent is extended or adjusted under 35 U.S.C. 154(b) by 0 days.

(21) Appl. No.: 09/381,536
(22) PCT Filed: Jan. 20, 1999
(86) PCT No.: PCT/FR99/00107
   § 371 Date: Sep. 21, 1999
   § 102(e) Date: Sep. 21, 1999
(87) PCT Pub. No.: WO99/38000
   PCT Pub. Date: Jul. 29, 1999

(30) Foreign Application Priority Data

Jan. 22, 1998 (FR) .................................. 98 00761

(51) Int. Cl.$^7$ ................................ G01J 3/48; G01N 31/12
(52) U.S. Cl. ........................ 422/82.02; 422/94; 422/55; 422/57; 422/70; 422/78; 422/80; 422/82.01; 422/82.05; 422/82.09; 422/91; 422/98
(58) Field of Search ................. 422/82.02, 94, 422/54, 55, 57, 70, 78, 80, 82.01, 82.05, 82.09, 91, 98; 250/288, 283, 341.6; 436/101, 124, 147, 149, 145

(56) References Cited

U.S. PATENT DOCUMENTS

| | | | |
|---|---|---|---|
| 3,607,096 | * 9/1971 | Hartmann | 422/54 |
| 3,860,345 | * 1/1975 | Raillere et al. | 356/315 |
| 4,097,239 | * 6/1978 | Patterson | 436/106 |
| 4,968,885 | * 11/1990 | Willoughby | 250/288 |
| 5,244,811 | * 9/1993 | Matthews | 436/146 |
| 5,246,868 | * 9/1993 | Busch et al. | 436/101 |
| 5,285,064 | * 2/1994 | Willoughby | 250/288 |
| 5,356,819 | * 10/1994 | Ritschel | 436/147 |
| 5,473,162 | * 12/1995 | Busch et al. | 250/341.6 |

* cited by examiner

*Primary Examiner*—Jill Warden
*Assistant Examiner*—Brian Sines
(74) *Attorney, Agent, or Firm*—William A. Drucker

(57) ABSTRACT

The invention concerns an apparatus comprising an intake scoop (2) for the gas sample to be analyzed and, coaxial to said scoop (2): two tubular sleeves (4) defining respectively an intake chamber (5) for an oxygen carrier gas opening into a first combustion chamber (8), and an intake chamber (11) for an oxidant gas opening into a second combustion chamber (9); a pair of electrodes (14) associated with a circuit (21) measuring the conductivity of a combustion zone located in the second combustion chamber (9) and focusing optics (19) focusing the image of the flame generated in the combustion chambers (8, 9) on the input orifice of a spectrophotometer (20); a processor (25) processes the data from the circuit (21) and from the spectrophotometer (20) to deduce therefrom the concentration in the searched elements. The invention is particularly useful for detecting sulphur, phosphorus and organic compounds.

7 Claims, 1 Drawing Sheet

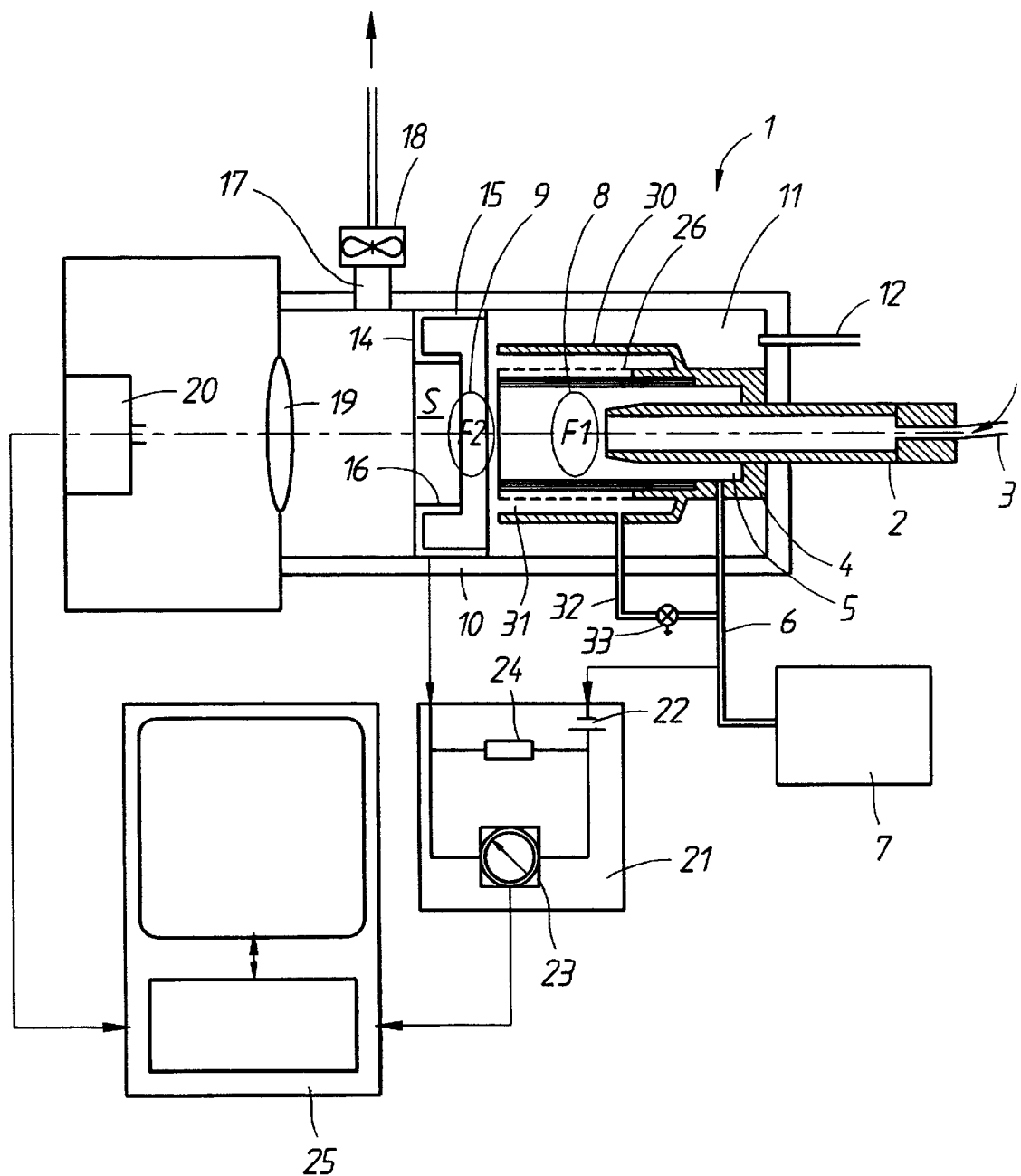

APPARATUS COMBINING SPECTROPHOTOMETRY AND FLAME IONISATION DETECTION FOR ANALYSING A GAS COMPOSITION

BACKGROUND OF THE INVENTION

The present invention concerns an apparatus for analyzing a gas composition combining spectrophotometry and flame ionization detection.

SUMMARY OF THE INVENTION

The invention particularly, but not exclusively, applies to the analysis of a gas composition in which the searched elements may also include elements generating light emissions characterizing for example sulfur, phosphorus, slightly emissive elements (even non-emissive) such as hydrocarbons.

It is generally known that flame spectrophotometry is a method for spectrographically analyzing radiation generated by the flame of a gas mixture including the elements to be analyzed and a combustive gas, such as hydrogen. Said analysis is carried out by isolating the radiations characterizing the searched elements and by measuring these radiations by photometric means. This method is particularly useful for detecting elements, such as sulfur, phosphorus, sodium and lithium.

So as to apply this process to certain elements not generating characteristic luminous emission, for example chlorine, it is necessary prior to combustion to make these elements react with a reactive element in order to obtain a compound generating a detectable or identifiable luminous emission.

Thus, as regards chlorine, the first reaction which aims at generating chlorides is carried by embodying a first combustion in a reducing medium in the presence of a reactive metal such as copper or indium, a gas mixture including hydrogen and the gas to be analyzed.

The gas mixture originating from said first combustion process is submitted to a second combustion process, but this time in an oxidizing medium which generates a light emission from which the spectrophotometric analysis is effected.

Similarly, the flame ionization detection (FID) analysis methods uses a burner in which the combustion of the sample to be analyzed in a combustive oxidant gas, such as hydrogen, is embodied in an oxidizing environment. Electrodes are therefore placed at the level of the combustion chamber of the burner so as to be able to measure the conductivity of the zone where combustion is generated.

Said measure makes it possible to detect the presence of combustible constituents in the sample and particularly organic matter, such as hydrocarbons or hydrocarbon derivatives. The combustion of this organic matter in fact produces between the measurement electrodes an ionization current in relation with the organic matter concentration. This method can be extended to a wider range of compounds by adding an agent, such as an alkaline salt which reacts with these compounds so as to ionize the gases to be analyzed.

It proves that analyses carried out by either of these methods may be altered by the presence of undesired compounds. Thus, for example the detection of chlorinated organic compositions may be altered for samples containing high concentrations of salt spray.

More particularly, the aim of the invention is to eliminate these drawbacks by using a high-performance analyzer able to be produced in the form of a portable and automatic device so as to conduct practically instantaneous analyses in situ.

According to the invention, the analyzer includes a tubular burner comprising at least one continuous intake nozzle for a gas sample to be analyzed, and coaxial to said nozzle:

a first tubular sleeve with a bottom traversed by said nozzle, this sleeve successively defining with said nozzle an annular chamber for admitting a combustive gas, such as hydrogen, derived from a source, then a first combustion chamber extending beyond the end of the nozzle, a second tubular sleeve with a bottom through which the nozzle traverses, said second sleeve successively defining with the first sleeve an annular chamber for admitting an oxidant gas such as air, and a second combustion chamber extending beyond the end of the first tubular sleeve, said second tubular sleeve including an opening for evacuating gases originating from combustion, a pair of electrodes associated with a circuit measuring the conductivity of a combustion zone located in the second combustion chamber, a focusing optic coaxial to said sleeves for focusing the image of the flame generated in at least the first combustion chamber on the input orifice of a spectrophotometric mounting.

Said apparatus includes in addition a processor able to process data delivered by the measurement circuit and/or the spectrophotometric mounting so as to deduce therefrom the concentration in the searched elements of the sample.

Advantageously, said pair of electrodes could include an annular electrode rendered integral with the second tubular sleeve so as to encircle at least partially the second combustion chamber : in this case, the first electrode could consist of the first tubular sleeve.

Of course, the first tubular sleeve could include at least at the level of its external surface a coating made of a suitable material able to emit a reactive gas under the effect of heat generated in the first combustion chamber. This coating could for example be made of indium so as to be able to detect chlorine.

In this case, the burner could include a third tubular coaxial sleeve defining with the first sleeve an annular chamber opening into the second combustion chamber and used for admitting a hydrogen current derived from said source. To this effect, this annular chamber is connected to this source via an intake circuit controlled by a valve.

By means of these dispositions, by combining the data supplied by these two analysis means (flame spectrophotometry/ionization), it is possible to significantly differentiate the number of searched elements or substances and especially resolve the problems of overlapping or masking of characteristic spectral lines of elements searched by others, even noise. Thus, it is possible to solve the problems of masking of hydrocarbonated chlorinated compounds by salt spray. In fact, it possible to determine the total concentration of sodium chloride by noting the concentration of sodium by means of spectrophotometry. To then obtain the concentration of the other chlorinated compounds, this sodium concentration is deducted from the total concentration of chlorine determined by means of the reactive gas emitted by the coating of the first tubular sleeve. The concentration of chlorinated organic compounds may then be determined from the data detected by the detection circuit FID (which determines the concentration of hydrocarbonated compounds).

BRIEF DESCRIPTION OF THE DRAWINGS

There now follows a description of a preferred embodiment method of the invention given by way of non-restrictive example with reference to the accompanying drawing in which:

The sole figure is a skeleton diagram of an analysis apparatus of the invention.

In this example, the analysis apparatus includes a tubular burner 1 comprising a tubular nozzle 2 connected on one side to a pipe 3 for admitting the gas to be analyzed and open on the other side and coaxial to said nozzle 2:

- a first tubular sleeve 4 with a diameter slightly greater than that of the nozzle 2 and axially offset with respect to the latter so as to delimit firstly with the nozzle 2 a first intake annular chamber 5 connected to a circuit 6 for injecting hydrogen derived from a source 7, and secondly beyond the first nozzle 2, a combustion chamber 8 in which the partial combustion of the gas to be analyzed and the hydrogen generates a first flame F1 : this first tubular sleeve 4 closes on one side on the nozzle 2 and opens on the other side into a second combustion chamber 9;
- a second tubular sleeve 10 with a diameter greater than that of the first tubular sleeve 4 and defining with the latter a second annular intake chamber 11 connected to an inlet circuit 12 for a gas or an oxidant gas mixture, for example air : this second sleeve 10 closes on one side on the nozzle 2 and/or on the second sleeve 4 and defines on the other side beyond the latter the second combustion chamber 9 in which a post-combustion is carried in an oxidizing environment of the gases originating from the first combustion chamber 8 and the intake chamber 11,
- an annular electrode 14, with an approximately inverted C section rendered integral via its face having a larger diameter 15 with the second sleeve 10 and whose face with a smaller diameter 16 which has an axial length smaller than that of the face 15, defines an outlet pipe S of the combustion chamber 9 : beyond the electrode 14 (on the side opposite the sleeve 4), the sleeve 11 includes a side orifice 17 into which an exhaust pipe opens equipped with a turbine 18 activated by a motor,
- focusing optics 19, such as a lens mounted in the circular opening of an inner capsule closing the sleeve 10 on the side opposite the nozzle 2, this focusing optic 19 being designed to focus the luminous radiation emitted in the two combustion chambers 8, 9, in particular the first chamber 8 on the input orifice or a spectrophotometric mounting 20.

In this example, the tubular sleeve 4 is made of an electrically conductive material and constitutes a second electrode which co-operates with the electrode 14 so as to allow measurement of the conductivity of the zone of the second chamber 9 in which the second flame (flame F2) is generated.

These two electrodes are electrically connected to the resistor measuring means 21, said means including a voltage source 22 series connected with a voltmeter 23, this unit being shunted by a resistor 24.

The data delivered by the spectrophotometer 20 and the voltmeter 23 are transmitted to a processor/display unit 25 programmed so as to determine the concentration of searched elements and/or substances of the gas sample brought by the nozzle 2.

As previously mentioned, the external surface of the sleeve 4 could be covered by a coating 26 made of a material able to emit a reactive gas at the temperature at which said sleeve 4 is brought under the effect of the combustion generated in the first combustion chamber 8. By way of example, this reactive material could consist of indium, the corresponding searched element then being chlorine.

In this case, the burner could include a third coaxial tubular sleeve 30 extending into the space inserted between the sleeves 4 and 10. This third sleeve 30 defines with the sleeve 4 an annular chamber opening into the second combustion chamber 9 and is used to admit into this chamber 9 a hydrogen current coming from the source 7. To this effect, the annular chamber 31 is connected to the source 7 by means of an intake circuit 32 controlled by a valve 33.

Functioning of said burner is then as follows

The two chambers 8, 9 are submitted to partial vacuum by the turbine 18 so as to suck in the gas to be sampled in the nozzle 2 through a faucet pipe provided in the intake circuit 3.

Inside the sleeve 4, the gas flow sucked-in (air, for example) mixes with the hydrogen current injected via the intake chamber 5 in such a proportion so that the combustion generated in the first combustion chamber 8 is reduced. The luminous radiation generated by the flame F1 in the first chamber 8 makes it possible to detect by means of a spectrophotometer mounting 20 compounds such as phosphorus and sulfur and deduce therefrom the searched elements.

The temperature generated by this combustion heats the sleeve 4 and, accordingly, the coating 26.

When it reaches or exceeds its vaporization temperature, the coating is 26 emits a reactive vapor which mixes with the flow of hydrogen injected via the intake chamber 31 and with the air coming from the intake chamber 11.

On leaving said chambers 11 and 31, the gas mixture reacts (oxidant combustion) with the gas flow resulting from the partial combustion produced in the chamber 8 to produce a flame F2 which emits a light characterizing a component such as chlorine which has reacted with the indium reactive vapor. Said light, as with the one produced in the chamber 8, is focused by the lens 19 at the inlet of the spectrophotometer 20.

The data delivered by the mounting 20 and also by the ammeter 23 (which are representative of the variations of conductivity of the flame (ionization) present in the second combustion chamber) are sent to the processor 25 which is programmed so as to interpret this information and deduce from it concentrations of the sought-after elements, whether they involve compounds, chemical substances or even biological substances (bacteria).

Of course, in the case of a gas sample to be analyzed contains suspended particles (for example bacteria or dust), these particles on burning generate limited light pulses (flash) able to count so as to obtain the number of particles per unit of gas volume to be analyzed.

Similarly, for the reasons mentioned previously, the burner could further include means for injecting into the second combustion chamber 9 an additive, such as an alkaline salt.

What is claimed is:

1. Apparatus combining spectrophotometry and the detection of the ionization of a flame for analyzing a gas composition, said apparatus including a tubular burner comprising at least one nozzle for continuously admitting a gas sample to be analyzed, and coaxially to this nozzle:
    a first tubular sleeve having a bottom traversed by said nozzle, this sleeve successively delimiting with said nozzle an annular chamber used for admitting a combustive gas, such as hydrogen originating from a source, then a first combustion chamber extending beyond the extremity of the nozzle, a second tubular sleeve having a bottom through which said nozzle passes, this second sleeve successively delimiting with the first sleeve an annular chamber for admitting an oxidizing gas, such as air, and a second combustion chamber, which extends beyond the extremity of the first tubular sleeve, this second tubular sleeve including an orifice for removing the gases originating from combustion, first and second electrodes electrically connected to a circuit for measuring the conductivity of a combustion zone located in the second chamber, wherein said first electrode comprises the first tubular element, and wherein said second electrode comprises an annular electrode rendered integral with the second tubular sleeve so as to encircle, at least partially, the second combustion chamber, focusing optics coaxial to each of the sleeves and designed to focus the image of the flame generated in at least the first combustion chamber on the input orifice of a spectrophotometric mounting, said apparatus further including a processor able to process the data delivered by the measurement circuit and/or the spectrophotometric mounting so as to deduce therefrom the composition and the concentration of the searched elements of the sample.

2. Apparatus according to one of the preceding claim 1, wherein the first tubular sleeve includes, at least at the level of the external surface a coating able to emit a reactive gas under the effect of the heat generated in the first combustion chamber.

3. Apparatus according to claim 2, wherein the coating is made of indium.

4. Apparatus according to claim 2, wherein the burner includes a third coaxial tubular sleeve defining with the first sleeve an annular chamber opening into the second combustion chamber for admitting an hydrogen current.

5. Apparatus according to claim 4, wherein the annular chamber is connected to the hydrogen source by means of an input circuit controlled by a valve.

6. Apparatus according to claim 1, comprising means for injecting into the second combustion chamber an additive element, such as an alkaline salt.

7. Apparatus according to claim 1, wherein in order to eliminate the noise signal generated by a salt spray in detecting chlorinated compounds, the processor is programmed so as to determine from the spectrophotometric data the sodium concentration of the sample, then deduct this concentration from the total concentration of chlorine.

* * * * *